(12) United States Patent
Kwok

(10) Patent No.: US 8,015,971 B2
(45) Date of Patent: Sep. 13, 2011

(54) METHOD AND APPARATUS FOR HUMIDIFICATION OF BREATHABLE GAS WITH PROFILED DELIVERY

(75) Inventor: Philip Rodney Kwok, Chatswood (AU)

(73) Assignee: ResMed Limited, Bella Vista (AU)

( * ) Notice: Subject to any disclaimer, the term of this patent is extended or adjusted under 35 U.S.C. 154(b) by 1222 days.

(21) Appl. No.: 11/658,336

(22) PCT Filed: Aug. 3, 2005

(86) PCT No.: PCT/AU2005/001156
§ 371 (c)(1),
(2), (4) Date: Jan. 24, 2007

(87) PCT Pub. No.: WO2006/015416
PCT Pub. Date: Feb. 16, 2006

(65) Prior Publication Data
US 2008/0302362 A1    Dec. 11, 2008

Related U.S. Application Data

(60) Provisional application No. 60/599,864, filed on Aug. 10, 2004.

(51) Int. Cl.
*A61M 16/00* (2006.01)
*A61M 16/16* (2006.01)
(52) U.S. Cl. ......... 128/204.17; 128/204.18; 128/204.21; 128/204.22; 128/204.23; 128/206.22
(58) Field of Classification Search ............. 128/206.22, 128/204.17, 204.18, 204.21, 204.22, 204.23
See application file for complete search history.

(56) References Cited

U.S. PATENT DOCUMENTS

| | | | | |
|---|---|---|---|---|
| 1,827,530 A * | 10/1931 | Le Grand | ........................ | 600/21 |
| 4,014,382 A * | 3/1977 | Heath | ............................. | 165/60 |
| 4,826,327 A * | 5/1989 | Michell | ........................... | 374/20 |
| 4,921,642 A * | 5/1990 | LaTorraca | ..................... | 261/142 |
| 5,165,398 A * | 11/1992 | Bird | ........................ | 128/204.25 |
| 5,769,071 A * | 6/1998 | Turnbull | .................. | 128/203.12 |
| 5,890,490 A * | 4/1999 | Aylsworth et al. | ....... | 128/203.12 |
| 6,152,129 A * | 11/2000 | Berthon-Jones | ......... | 128/200.24 |
| 6,165,131 A * | 12/2000 | Cuce' et al. | .................... | 600/495 |
| 6,240,921 B1 * | 6/2001 | Brydon et al. | ........... | 128/205.23 |
| 6,272,933 B1 * | 8/2001 | Gradon et al. | .................. | 73/861 |
| 6,397,841 B1 * | 6/2002 | Kenyon et al. | ........... | 128/202.27 |
| 6,554,260 B1 * | 4/2003 | Lipscombe et al. | .......... | 261/142 |

(Continued)

FOREIGN PATENT DOCUMENTS

DE    103 18 383    7/2004

(Continued)

OTHER PUBLICATIONS

International Search Report for PCT/AU2005/001156 mailed Sep. 7, 2005.

(Continued)

*Primary Examiner* — Justine R Yu
*Assistant Examiner* — Clinton Ostrup
(74) *Attorney, Agent, or Firm* — Nixon & Vanderhye P.C.

(57) ABSTRACT

A method and apparatus for delivering breathable gas to a user includes a humidifying unit that is controllable to humidify the gas in accordance with a variable humidity profile such that the gas is delivered to the user at variable humidity levels, e.g., during a treatment session.

11 Claims, 2 Drawing Sheets

U.S. PATENT DOCUMENTS

| | | | |
|---|---|---|---|
| 6,584,972 B2 * | 7/2003 | McPhee | 128/203.17 |
| 6,626,175 B2 * | 9/2003 | Jafari et al. | 128/204.21 |
| 6,668,829 B2 * | 12/2003 | Biondi et al. | 128/204.21 |
| 7,137,388 B2 * | 11/2006 | Virr et al. | 128/203.17 |
| 7,306,205 B2 * | 12/2007 | Huddart et al. | 261/130 |
| 7,478,635 B2 * | 1/2009 | Wixey et al. | 128/203.17 |
| 7,516,740 B2 * | 4/2009 | Meier | 128/203.16 |
| 2004/0016430 A1 * | 1/2004 | Makinson et al. | 128/203.12 |
| 2004/0055597 A1 | 3/2004 | Virr et al. | |
| 2004/0221844 A1 * | 11/2004 | Hunt et al. | 128/204.17 |

FOREIGN PATENT DOCUMENTS

| | | |
|---|---|---|
| EP | 535952 A1 * | 4/1993 |
| EP | 762107 A1 * | 3/1997 |
| EP | 0 885 623 A2 | 12/1998 |
| EP | 1 329 240 | 7/2003 |
| GB | 2 338 420 | 12/1999 |
| JP | 09-234347 | 9/1997 |
| JP | 11-57009 A | 3/1999 |
| JP | 2001-000553 | 1/2001 |
| WO | 01/13981 | 3/2001 |
| WO | WO 02/066106 A1 | 8/2002 |
| WO | WO 02066107 A1 * | 8/2002 |
| WO | 03/018096 | 3/2003 |
| WO | 2004/020031 | 3/2004 |
| WO | 2004/039444 | 5/2004 |

OTHER PUBLICATIONS

Notice of Reasons for Rejection mailed Nov. 30, 2010 in Japanese Appln. No. 2007-525125, with English translation.

* cited by examiner

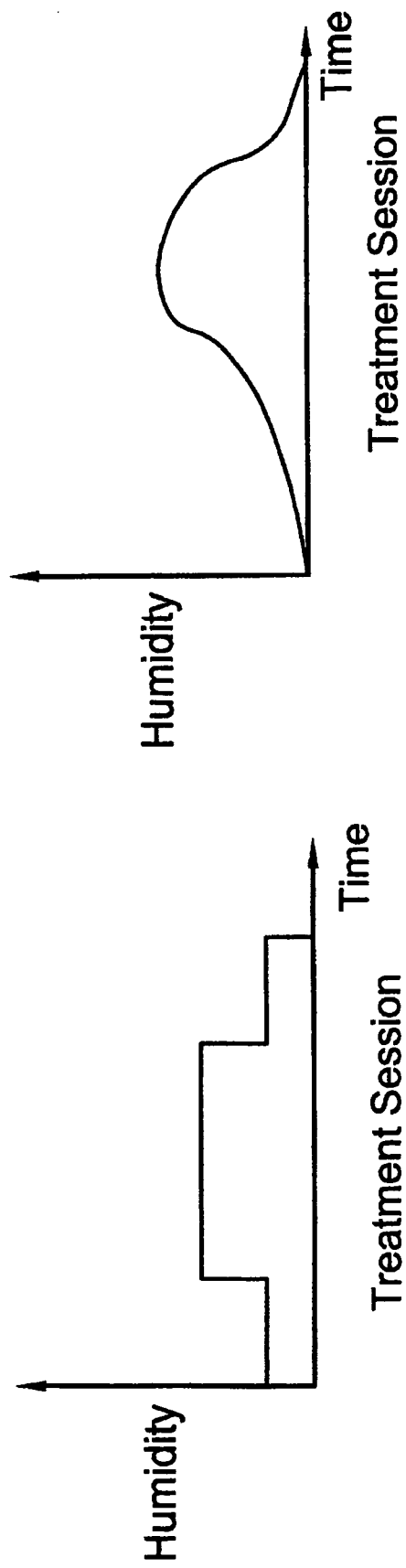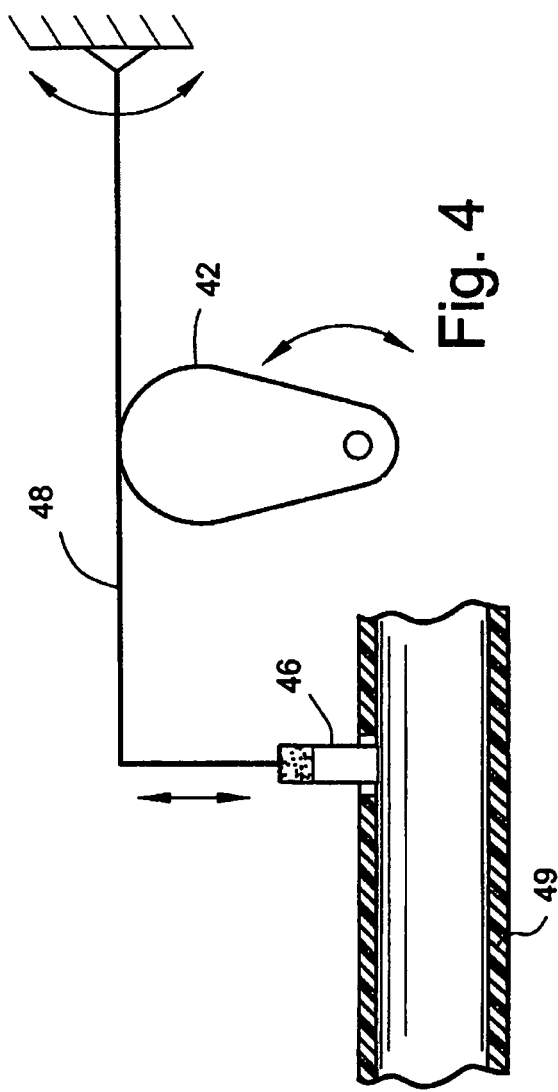

METHOD AND APPARATUS FOR HUMIDIFICATION OF BREATHABLE GAS WITH PROFILED DELIVERY

CROSS-REFERENCE TO RELATED APPLICATIONS

This application is the US national phase of international application PCT/AU2005/001156 filed 3 Aug. 2005, which designated the U.S. and claims the benefit of U.S. Provisional Application No. 60/599,864, filed Aug. 10, 2004, each of which is incorporated herein by reference in its entirety.

STATEMENT REGARDING FEDERALLY SPONSORED RESEARCH OR DEVELOPMENT

None.

BACKGROUND OF THE INVENTION

Many humidifiers that are currently manufactured for patient respiratory disorders such as Obstructive Sleep Apnea (OSA) are large, bulky, and have large water reserves to treat most medical-related ailments such as dryness that may be caused by mouth leaks for example. Mouth leaks or any leaks for that matter release humidified gases to the atmosphere and bypasses the patient's airways where it is required. These heavy requirements including those medical conditions requiring high levels of continuous humidification may require humidifier devices with reserves as high as 600 mL of water. This increases the overall size and bulk of the Continuous Positive Airway Pressure (CPAP) Apparatus, ventilator, patient breathing air system, or gas supply system.

Where patients do not exhibit these inadvertent leaks or are only seeking lower levels of humidification, they are likely to be left with an unnecessarily oversized reservoir of remaining water at the end of a treatment session.

Furthermore, there are a substantial number of patients that only require relatively smaller amounts of humidification to marginally improve comfort to an acceptable level for a typical patient. These patients for example may include those that only use their conventional humidifiers (ResMed HUMID-AIRE™ or Fisher & Paykel HC100™) during the cooler months in winter for small but substantial gain in comfort by adding warmth and/or moisture to the airways that may dry due to the flow of air through the patient airways.

Current humidifiers are generally designed to fulfill the worst ailments and therefore require substantial humidification requirements. These systems could be regarded as 'overkill' for a substantial population of OSA patients who are only looking for a 'comfortable' level of improvement to undesirable dry and cool air.

Current and conventional humidification systems generally supply a continuous level of humidification as set by the user and dependent on the ambient temperature and humidity level. There are also systems that may modify humidification levels using a number of sensor arrays such as temperature sensors and/or humidity or flow sensors in aid to maximize efficiency and/or synchronize with pressure or airflow. These conventional systems can maximize the performance of the humidifier by being able to deliver the maximum amount of humidity whilst reducing or eliminating condensation (e.g. cooler air can carry less moisture), also known in the art as "rain-out". However, these types of sensor systems are complex and costly and still consume large amounts of water.

Accordingly, a need has developed in the art to address at least one of the shortcomings of the prior art humidifiers described above.

BRIEF SUMMARY OF THE INVENTION

One aspect of the invention to ameliorate the size and design constraints of the conventional humidifier whilst delivering an adequate and comfortable level of humidification whilst consuming/delivering the fluid (e.g. water, core gas vapor, etc.) in an efficient manner (requiring lower liquid reservoir volumes) and delivered according to the patient's needs, which may also be a manually selectable and/or programmable, semi-automated and/or automated delivery profile.

Another aspect of the invention relates to assisting patients looking for limited improvement to breathing comfort. However, the intention is not to replace conventional, continuously heated humidifiers, but rather to provide an additional choice more suitable for certain patients.

Another aspect of the invention provides profiled delivery of humidified gas to a patient.

Another aspect of the invention reduces water or fluid volume required by maximizing efficient use of water, which is a form of 'rationing'.

Another aspect of the invention aims to improve breathing comfort according to patient selectable profiles in one embodiment.

These and other aspects will be described in or apparent from the following detailed description.

BRIEF DESCRIPTION OF THE DRAWINGS

FIGS. 2 and 3 illustrate sample humidity profiles for a patient's treatment session; and FIG. 4 schematically illustrates an alternative embodiment of the present invention.

DETAILED DESCRIPTION OF PREFERRED EMBODIMENTS

Figure 1:
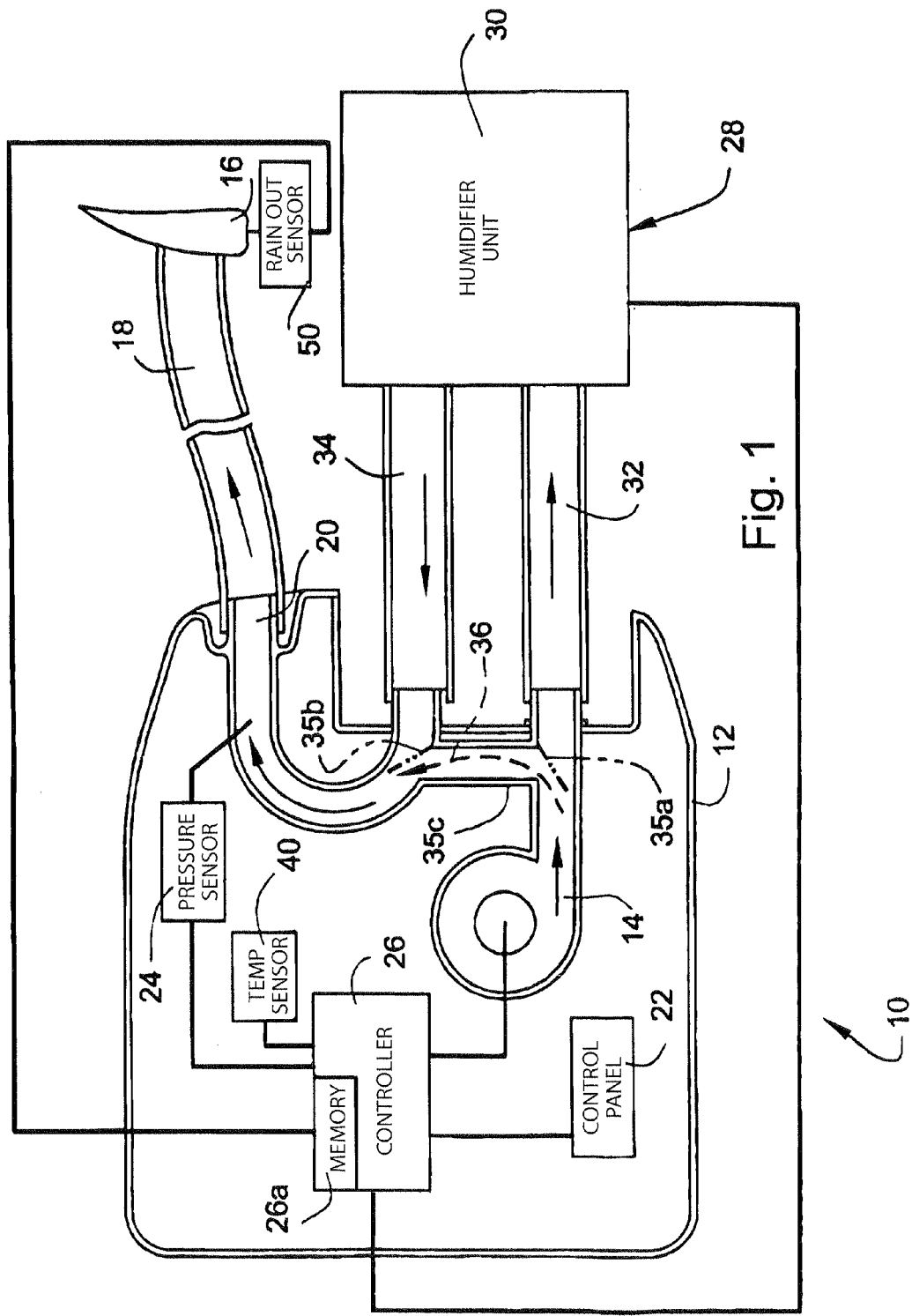
FIG. 1 is a schematic view of a blower according to an embodiment of the present invention.

FIG. 1 schematically illustrates a blower 10 according to an embodiment of the present invention. Blower 10 typically includes a housing 12 to support a blower motor 14 that pressurizes breathable gas for delivery to a patient interface 16 (e.g., a mask) via an air delivery conduit 18 that is connected to an outlet conduit 20 of blower 10. Blower 10 includes a control panel 22 with one or more buttons and preferably a display. Blower 10 includes a pressure sensor 24 to provide a signal to a controller 26 (e.g., CPU) for control of blower motor 14, in accordance with one or more control algorithms commercially available from ResMed, Inc.

Blower 10 is optionally provided with a selectively attachable and detachable humidifier unit 28 that includes a tub 30 and one or more conduits 32, 34 that communicate with blower 10. Humidifier unit 28 may include structure as detailed in U.S. Published Patent Application No. 2004/0055597A1, incorporated by reference in its entirety. Humidifier unit 28 is in communication with controller 26, e.g., when conduits 32, 34 are attached to blower 10.

In one embodiment, the operation and/or performance of the humidifier unit 28 is tailored or profiled to suit the patient's specific humidification requirements. This in turn results in more efficient water usage, and allows the capacity of the tub 30 to be reduced. For example, the capacity of the tub 30 can be less than 400 mL, e.g., from 20 mL-400 mL or more preferably between 50 mL-200 mL. Of course, the volume capacity can be greater or less, depending on application. This reduced volume allows the overall size of the blower humidifier and/or assembly to be reduced, thereby removing design constraints and facilitating transport of the blower, e.g., during travel of the patient.

Profiling may be intermittent or profiled in accordance to a patient selectable profile or according to a selectable or semi/automated profile typical of the treatment session's ambient environment conditions.

Another embodiment may modify the delivery profile according to temperature of room over the course of a treatment session. The device may measure temperature versus time and predict what adjustments in profile are desirable to maintain efficient fluid/water use.

In another embodiment the profile may change over a set time period of treatment. For example, during an eight-hour treatment session, the profile begins at start of treatment and continues on to either end of session or a set time period on the device.

The above can obviously be used in combination with other embodiments such as watching average room temperature or even monitoring temperature changes over a period of hours, days, weeks, or months, and can modify the profile accordingly.

A profile may, for example, recognize that a typical bedroom tends to cool until the early hours of the morning where the temperature tends to stabilize before warming again by sunrise. Another profile that may be used may gradually reduce the humidity level during the course of the night in one simple form of the invention.

In embodiments, the invention may also postpone delivery until a period of the sleep session has passed. For example, a patient in the case of CPAP does not tend to go to sleep (beginning of treatment session) with dry airways. Their airways are probably going to dry later, say one hour into the night. Compared to conventional humidifiers used in OSA over eight-hour sessions, this feature alone can reduce humidification water volumes by one-eighth.

When implementing the delay feature, valves 35a and 35b can be used to divert the path of the air so as to by-pass the humidifier unit 28 via a by-pass conduit 35c. The air path is schematically illustrated in FIG. 1 with a broken arrow 36. When shut, valves 35a and 35b form part of the respective walls of gas conduits within blower 10.

The invention in one preferred embodiment may cycle between switch on and off during the course of the night. These cycles can be regular, irregular, or otherwise controlled for numerous intervals and various durations using some smart electronic control. The switching off does not necessarily need to completely switch off, but may reduce in temperature during periods where less humidification is required. As mentioned, this reduces water usage but may also lead to reduced energy (power) consumption and/or reduced running costs. For example, humidifier unit 28 may include a heater element to heat the volume of water. Heater element can be controlled via controller 26.

A user's manually selectable version is also possible. For example, as shown in FIGS. 2 and 3, a patient may set the humidifier device from a menu including, e.g., a Square wave or a Sinusoidal wave which may be integrated into blower 10 or humidifier unit 28 in the form of a symbol on a dial or push button. The device then humidifies the air to a level according to these changing profiles over a treatment session. In the case of a Sinusoidal wave setting where the cycle starts as a 'rise', the humidifier level increases gradually to a maximum during the middle of a treatment session and gradually reduces to the end of the treatment session. The profile can be symmetrical or asymmetrical. Also, the delay feature described above can be used in conjunction with the Square and/or Sinusoidal wave, so that humidity is added only after treatment has commenced.

If the humidifier provides instantaneous humidification on demand, this profile may also be adapted on a patient breath-by-breath basis rather than over a full treatment session.

These profiles mentioned above can be any combination or variation of a wave/curve and/or stepped. It may also be automated to learn the ambient environmental conditions. For example, a temperature sensor 40 (FIG. 1) may monitor room temperature changes over the annual seasons and modify the profile further to gain maximum water/fluid use and efficiency. For example, during cooler months, the humidification profile may allow for longer humidification periods (during the switch on or higher heat cycle) but not allow as high a level so as to reduce condensation and maximize comfort for the patient.

Another embodiment may include a 'fuzzy logic' version where the user, with the assistance of the device's intelligence, provides an optimum humidification profile, which provides optimal comfort to the patient whilst maintaining efficient fluid/water usage. In this example, the patient may wake up and press one of three buttons, or select a dial setting, to indicate whether the level of humidification was "okay", "too little" or "too much". The device can then re-profile the delivery according to the patient's perceived comfort level. In this case, much of the actual profiling is automated.

Another embodiment of the invention considers two positive aspects of humidification and provides additional benefits. Current technology warms the patient breathing air. Warm air is considered more comfortable to breathe especially if the ambient temperature is relatively low. Secondly, humidifiers add moisture to the breathing air. The invention may profile the humidity level at a different rate to that of the air temperature. For example, according to the Sinusoidal wave setting example mentioned earlier, the device may maintain warm breathing air with minimal increased requirement at the middle of the treatment session. The humidity however may increase at an independent level relative to the temperature; for example, the humidity may increase much more than the temperature at the peak of the wave profile. This can again be selected by a patient according to their comfort requirements.

Any of the embodiments mentioned above may have an ability to transfer any 'learned' logic by memory storage media, or wireless communication (e.g. "Blue tooth" technology) so that the logic could be utilized by a physician, another user, or else simply because the patient intends to replace the device or upgrade to a newer model. Controller 26 may include a memory 26a to facilitate data storage/transfer.

In a more mechanized embodiment of the invention, a simple valve that controls the humidified air entering the mainstream breathing air may be controlled by mechanical links. For example, as shown in FIG. 4, a rotating cam 42 that is profiled to control a valve 46 via mechanical linkage 48, thus producing staged delivery of humidified gas through a conduit 49 (which may be conduit 34 in FIG. 1). The cam profile can be such that the peak of the cam's lobe translates to largest valve opening and therefore greatest humidification level. The cam 42 could be designed to turn one revolution in one treatment session. The shape of the cam lobe determines the delivery profile. A bimetallic spring may also be added to modify lift (generally reduce lift to reduce humidification as temperature decreases) and therefore forms a type of mechanical temperature compensation.

Further to the above embodiment, the profile could be mechanically adjustable by a user. For example, a number of selectable pins around the perimeter of a cam lobe could be push in or out to modify at what period of the session and by how much to lift the valve.

In another embodiment, the invention may also incorporate a switch or sensor device that switches off the humidifier should the treatment session be interrupted. For example, an OSA patient may get up in the middle of the night to go to the bathroom. This feature is designed to reduce water consumption further and also prevent condensation in the air delivery pipe, especially if the flow generator has stopped (ResMed's Smart Stop™ feature). It may also prevent the patient breathing in condensate when they return to bed, which in turn improves patient comfort.

Yet another embodiment of the invention includes a mask "rain-out" sensor 50 (FIG. 1) that does not require the use of humidity sensor like the prior art. An infrared emitter and detector in communication with controller 26, e.g., are placed at the bottom of the mask interface or location where condensation is likely to bead or pool. The mask frame wall in front of the side-by-side emitter/detector is transparent to infrared light. Under normal conditions, the detector does not see any infrared light. If significant water droplets develop (condensation) in front of the emitter/detector, the light reflects back to the detector and signifies condensation. The device may also use another type of visible or non-visible light emitter/detector combination.

The above feature applied to the invention may either reduce humidification or heating in response to "rain-out", or otherwise it may modify the humidification delivery profiles as described earlier to improve patient comfort. Also by identifying "rain-out", this may provide intelligence to the device's control that the ambient temperature is falling or the heating of the delivered air is too low to carry the current level of moisture.

One or more of the following advantages may be realized in accordance with preferred embodiments of the invention:

Humidifier that is smaller, easier to store or travel with.

A device that can be tailored (profiled) or set by a user to suit their circumstances, needs or desires for comfort.

A profile humidifier may bridge the gap between inefficient "Passover" (non-heated) humidifiers and fully featured heated humidifiers that treat most dry airway ailments.

Potentially less complaints of "rain-out" or condensation as patients may have adjusted their device to a high setting, only to find that a cooling room creates increased condensation.

Ability to control, modify and fine-tune their patient's therapy.

By minimizing humidity delivery when it is not necessary reduces water usage and reservoir volume required, therefore reducing device size.

Alleviates the size constraints on engineers for the OSA market that is trending towards fewer design compromises to meet comfort expectations.

Flow generators have already been reduced in size, whereas the humidifier is about the same size as next generation flow generators, if not larger. This concept gives users the perception of even more compact dimension that is potentially lighter and easier to transport.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the invention. For example, the above described preferred embodiments of the invention may be adapted to any humidification device whether to treat OSA or used in any gas breathing system.

The invention claimed is:

1. A method for delivering breathable gas to a user, comprising: positively pressurizing the gas to a predetermined level using a blower; humidifying the breathable gas in accordance with a humidity profile having a variable humidity level using a humidifier, wherein the humidity profile is stored in the blower or the humidifier; delivering to the user the breathable gas with the variable humidity level using a user interface; selecting the humidity profile from a menu on the blower or humidifier; and changing the humidity profile in accordance with ambient environmental conditions.

2. The method according to claim 1, wherein the menu includes a sinusoidal wave humidity profile, a square wave humidity profile, or a combination thereof.

3. The method according to claim 1, wherein the menu includes humidity acceptability indicators that indicate whether to change the humidity profile, and the method further comprises changing the humidity profile based on fuzzy logic.

4. The method according to claim 1, wherein the ambient environmental conditions include at least one of temperature and humidity.

5. The method according to claim 4, further comprising adjusting the temperature and the humidity of the gas delivered to the user independently of one another.

6. The method according to claim 1, further comprising interrupting the humidifying of the gas if the delivery of the gas to the user ceases.

7. The method according to claim 1, further comprising sensing condensation in the user interface.

8. The method according to claim 7, wherein the sensing includes using an infrared emitter/detector arrangement to detect condensation.

9. The method according to claim 7, further comprising adjusting the temperature of the breathable gas based on the sensing of condensation.

10. The method according to claim 1, further comprising delaying the humidifying of the breathable gas for a predetermined period of time after the user's treatment session has commenced.

11. The method according to claim 1, further comprising cycling the variable humidity levels during the user's treatment session.

* * * * *